United States Patent [19]

Tyers

[11] Patent Number: 4,845,115
[45] Date of Patent: Jul. 4, 1989

[54] METHOD OF MEDICAL TREATMENT

[75] Inventor: Michael B. Tyers, Ware, England

[73] Assignee: Glaxo Group Limited, London, United Kingdom

[21] Appl. No.: 133,884

[22] Filed: Dec. 16, 1987

[30] Foreign Application Priority Data

Dec. 17, 1986 [GB] United Kingdom ................ 8630075
Nov. 11, 1987 [GB] United Kingdom ................ 8726424

[51] Int. Cl.$^4$ ............................................ A61K 31/415
[52] U.S. Cl. .................................................... 514/397
[58] Field of Search ........................................ 514/397

[56] References Cited

FOREIGN PATENT DOCUMENTS 2153821A 8/1985 United Kingdom .

Primary Examiner—Stanley J. Friedman
Attorney, Agent, or Firm—Bacon & Thomas

[57] ABSTRACT

The invention relates to the use of 1,2,3,9-tetrahydro-9-methyl-3-[(2-methyl-1H-imidazol-1-yl)methyl]-4H-carbazol-4-one and physiologically acceptable salts and solvates thereof in the treatment of cognitive disorders such as attentional and memory deficits and dementia states.

6 Claims, No Drawings

METHOD OF MEDICAL TREATMENT

This invention relates to a new medical use for a heterocyclic compound and pharmaceutical compositions containing it. In particular it relates to the use of 1,2,3,9,-tetrahydro-9-methyl-3-[(2-methyl-1H-imidazol-1-yl)methyl]-4H-carbazol-4-one and the physiologically acceptable salts and solvates thereof in the treatment of dementia and other cognitive disorders.

The aforementioned compound may be represented by the formula (I):

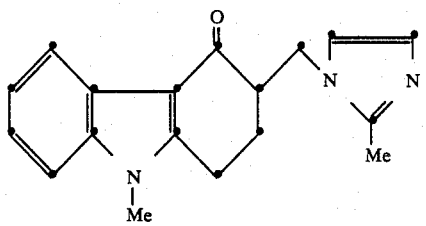

and is disclosed in UK Patent Specification No. 2153821a.

Suitable physiologically acceptable salts of the compound of formula (I) include acid addition salts formed with organic or inorganic acids for example, hydrochlorides, hydrobromides, sulphates, phosphates, citrates, fumarates and maleates. The solvates may, for example, by hydrates.

The aforementioned specification also discloses physiologically acceptable equivalents of the compound of formula (I), i.e. physiologically acceptable compounds which are converted in vivo into the parent compound of formula (I).

The compound of formula (I) is described in the aforementioned specification as a potent and selective antogaonist of 5-hydroxytryptamine (5-HT) at 'neuronal' 5-HT receptors of the type located on terminals of primary afferent nerves. Receptors of this type are now designated as 5-HT$_3$ receptors and are also present in the central nervous system. 5-HT occurs widely in the neuronal pathways in the central nervous system and disturbance of these 5HT containing pathways is known to alter behavioural syndromes such as mood, psychomotor activity, appetite and memory.

The compound is described as being of use in the treatment of a human or animal subject suffering from a condition caused by a disturbance of neuronal 5-HT function, for example in the treatment of a human subject suffering from migraine pain or a psychotic disorder such as schizophrenia. It is also stated that the compound may be useful in the treatment of conditions such as anxiety, obesity and mania.

We have now found that the compound of formula (I) may be useful in the treatment of cognitive disorders such as attentional and memory deficits and dementia states. These types of condition occur in, for example, senile dementia of the Alzheimers type, ageing, cerebrovascular deficiency and Parkinson's disease.

The effectiveness of the compound of formula (I) for use in the treatment of cognitive disorders has been demonstrated in rats in the spontaneous alternation test, and in marmosets given learning tasks in the Wisconsin General Test Apparatus.

Accordingly the invention provides a method of treatment of a subject, in particular a human subject, suffering form dementia or another cognitive disorder, which comprises administering to the subject an effective amount of a compound of formula (I) or a physiologically acceptable salt or solvate thereof.

References in this specification to treatment include prophylactic treatment as well as the acute alleviation of symptoms.

A preferred form of the compound of formula (I) is the hydrochloride, particularly in a hydrated form (e.g. the dihydrate).

In a further aspect, the invention provides a pharmaceutical composition which comprises an effective amount of the compound of formula (I), or a physiologically acceptable salts or solvate (e.g. hydrate) thereof, for use in medicine, particularly human medicine, for the treatment of dementia and other cognitive disorders.

In a yet further aspect, the invention provides for the use of the compound of formula (I) or a physiologically acceptable salt or solvate thereof, for the manufacture of a medicament for the treatment of dementia and other cognitive disorders.

Pharmaceutical compositions for use in accordance with the present invention may be formulated in conventional manner using one or more physiologically acceptable carries or excipients.

Thus the compound of formula (I) and is physiologically acceptable salts and solvates may be formulated for oral, buccal, parenteral, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipietns such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxygenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compound of formula (I) may be formulated for parenteral administration by injection e.g. by bolus injection or continuous infusion. Formulations for injection may be presented in unit dosage form e.g. in ampules or in multi-dose containers, with an added preservative. The compositions may taken such forms as suspensions solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compound of formula (I) may also be formulated in rectal compositions such as suppositories or retention enemas, e.g. containing conventional suppository bases such as cocoa butter or other glycerides.

In addition to the formulations described previously, the compound may also be formulated as a depot preparation. Such long acting formulations may be administered by implantation (for example subcutaneously, transcutaneously or intramuscularly) or by intramuscular injection. Thus, for example, the compound of formula (I) may be formulated with suitable polymeric or hydrophobic materials (for exmaple as an emulsion in an acceptable oil) or ion exchange resins, or as sparingly soluble derivatives, for example, as a sparingly soluble salts.

A proposed dose of the compound of formula (I) for administration to a human (of approximately 70kg body weight) is 0.05 $\mu$g to 20 mg, for example 0.05 mg to 20 mg, or 0.1 to 10 mg, of the active ingredient per unit dose, expressed as the weight of free base. The unit dose may be administered, for example, 1 to 4 times per day. A more preferred dose of active ingredient per unit does is 0.05 $\mu$g to 1mg. The dose will depend on the route of administration. It will be appreciated depending on the age and weight of the patient as well as the severity of the condition to be treated.

The compound of formula (I) may be prepared by the processes described in UK Patent Specification No. 2153821A and the following examples illustrate its preparation and salt formation. Temperatures are in ° C.

EXAMPLE 1

1,2,3,9-Tetrahydro-9-methyl-3-[)2-methyl-1H-imidazol-1-yl)methyl]-4H-carbazol-e-one A solution of 3-[(dimethylamino)methyl]-1,2,3,9-tetrahydro-9-methyl-4Hcarbazol-4-one hydrochloride (1.7g) in water (17 ml) was treated with 2-methylimidazole (1.4g) and then heated under reflux for 20h. The cooled mixture was filtered and the residue washed with water (3×15ml) to give a product (1.7g) m.p. 221°–221.5°. This material was recrystallized from methanol to give the title compound (1.4g) m.p. 231°–232°.

EXAMPLE 2

1,2,3,9-Tetrahydro-9-methyl-3-[(2-methyl-1H-imidazol-1-yl)methyl]-4H-carbazol-4-one hydrochloride dihydrate 1,2,3,9,-Tetrahydro-9-methyl-3-[(2-methyl-1H-imidazol-1-yl)methyl]-4H-carbazol-4-one (18.3g) in a hot mixture of isopropanol (90ml) and water (18.3ml) was treated with concentrated hydrochloric acid (6.25ml). The hot mixture was filtered and the filtrate diluted with isopropanol (90ml) and stirred at room temperature for 17h, cooled to 2° and the solid filtered off (21.6g). A sample (6g) was recrystallized from a mixture of water (6ml) and isopropanol (10ml) to give the title compound as a white crystalline solid (6g) m.p. 178.5°–179.5°.

Analysis Found: C,59.45;H,6.45;N,11.5. $C_{18}H_{19}N_3O.HCl.2H_2O$ requires C,59.1;H,6.6;N,11.5%.

Water assay Found: 10.23% $C_{18}H_{19}N_3O.HCl.2H_2O$ requires 9.855

The following examples illustrate pharmaceutical formulations for use according to the invention, containing 1,2,3,9-tetrahydro-9-methyl-3-[(2-methyl-1H-imidazol-1-yl)methyl]-4H-carbazol-4-one hydrochloride dihydrate as the active ingredient (1.25g of the hydrochloride dihydrate contains 1.00g of the free base).

TABLETS FOR ORAL ADMINISTRATION

Tablets may be prepared by the normal methods such as direct compression or wet granulation.

The tablets may be film coated with suitable film fomring materials, such as hydroxypropyl methylcellulose, using standard techniques. Alternatively the tablets may be sugar coated.

| | Direct Compression Tablet | mg/tablet |
|---|---|---|
| (i) | Active Ingredient | 4.688 |
| | Calcium Hydroqen Phosphate BP* | 83.06 |
| | Croscarmellose Sodium NF | 1.8 |
| | Magnesium Stearate BP | 0.45 |
| | Compression weight | 90.0 |

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5mm, flat bevelled edge punches.

| | | mg/tablet |
|---|---|---|
| (ii) | Active Ingredient | 0.3125 |
| | Anhydrous Lactose USNF | 131.99 |
| | Pregelatinised Starch USNF | 7.0 |
| | Maqnesium Stearate 8P | 0.7 |
| | Compression weight | 140.0 |

The active ingredient is passed through a 60 mesh sieve , and blended with the lactose, pregelatinised starch and magnesium stearate. The resultant mix is compressed into tablets using a Manesty F3 tablet machine fitted with 7.5mm normal concave punches.

| Sub-Lingual Tablet | mg/tablet |
|---|---|
| Active Ingredient | 2.5 |
| Compressible Sugar NF | 62.0 |
| Magnesium Stearate BP | 0.5 |
| Compression Weight | 65.0 |

The active ingredient is sieved through a suitable sieve, blended with the excipients and compressed using suitable punches.

| Wet Granulation Conventional Tablet | mg/tablet |
|---|---|
| Active Ingredient | 2.5 |
| Lactose BP | 151.0 |
| Starch BP | 30.0 |
| Pregelatinised Maize Starch BP | 15.0 |
| Magnesium Stearate BP | 1.5 |

-continued

| Wet Granulation | |
|---|---|
| Conventional Tablet | mg/tablet |
| Compression Weight | 200.0 |

The active ingredient is sieved through a suitable sieve and blended with lactose, starch and pregelatinised maise starch. Suitable volumes of purified water are added and the powders are granulated. After drying, the granules are screened and blended with the magnesium stearate. The granules are then compressed into tablets using 7mm diameter punches.

| Sub-Lingual Tablet | mg/tablet |
|---|---|
| Active Ingredient | 2.5 |
| Mannitol BP | 56.5 |
| Hydroxypropylmethylcellulose | 5.0 |
| Magnesium Stearate BP | 1.0 |
| Compression Weight | 65.0 |

The active ingredient is sieved through a suitable sieve and blended with the mannitol and hydroxypropylmethylcellulose. Suitable volumes of purified water are added and the powders are granulated. After drying, the granules are screened and blended into tablets using suitable punches.

Tablets of other strengths may be prepared by altering the ratio of active ingredients to excipients or the compression weight and using punches to suit.

| CAPSULES | mg/capsule |
|---|---|
| Active Ingredient | 2.5 |
| *Starch 1500 | 96.5 |
| Magnesium Stearate BP | 1.0 |
| Fill Weight | 100.0 |

*a form of directly compressible starch.

The active ingredient is sieved and blended with the excipients. The mix is filled into size No. 2 hard gelatine capsules using suitable machinery. Other doses may be prepared by altering the fill weight and if necessary changing the capsule size to suit.

SYRUP

This may be either a sucrose or sucrose free presentation.

| A. Sucrose Syrup | mg/5 ml dose |
|---|---|
| Active Ingredient | 2.5 |
| Sucrose BP | 2750.0 |
| Glycerine BP | 500.0 |
| Buffer | |
| Flavour | |
| Colour | as required |
| Preservative | |
| Purified Water BP to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup is clarified by filtration.

| B. Sucrose-Free | mg/5 ml dose |
|---|---|
| Active Ingredient | 2.5 |
| Hydroxypropylmethylcellulose USP (viscosity type 4000) | 22.5 |
| Buffer | |
| Flavour | |
| Colour | as required |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

INJECTIONS

The injection may be administered by the intravenous or subcutaneous route.

| | | $\mu$g/ml |
|---|---|---|
| (i) | Active Ingredient | 800 |
| | Dilute Hydrochloric Acid BP | to pH 3.5 |
| | Sodium Chloride Injection BP | to 1 ml |

The active ingredient is dissolved in a suitable volume of Sodium Chloride Injection BP, the pH of the resultant solution is adjusted to pH3.5 with dilute hydrochloric acid BP then the solution is made to volume with sodium choride injection BP and thoroughly mixed. The solution is filled into Type 1 clear glass 5 ml ampoules which are sealed under a headspace of air, by fusion of the glass then sterilised by autoclaving at 120° for not less than 15 minutes.

| | | mg/ml |
|---|---|---|
| (ii) | Active ingredient | 0.0625 |
| | Citric Acid Monohyrate BP | 0.50 |
| | Sodium Citrate BP | 0.25 |
| | Sodium Chloride BP | 9.00 |
| | Water for Injections USP to | 1.0 ml |

The citric acid monohydrate, active ingredient, sodium citrate and sodium chloride are dissolved in the major portion of the water for injections, the solution is made to volume and mixed thoroughly. After filtration, the solution is filled under air into ampoules which are sealed by fusion of the glass. The ampoules are sterilised by autoclaving for at least 15 minutes at 121°-124° C.

| SUPPOSITORY | |
|---|---|
| Active Ingredient | 5.0 mg |
| *Witepsol H15 to | 1.0 g |

*Witepsol H15 is a proprietary grade of Adeps Solidus Ph Eup.

A suspension of the active ingredient is prepared in the molten Witepsol and filled, using suitable machinery, into 1g size suppository moulds.

The efficacy of the compound of formula (I) in the treatment of cognitive disorders has been demonstrated in rats in the spontaneous alternation test, and in marmosets given learnign tasks in the Wisconsin General Test Apparatus.

TEST COMPOUND
1,2,3,9-Tetrahydro-9-methyl-3-[)2-methyl-1H-imidazol-1-yl)methyl]-4H-carbazol-4-one hydrocloride dihydrate.

RAT SPONTANEOUS ALTERNATION TEST

Introduction

This model is based on the tendency of rats to explore their environment. Each rat is given two runs in a T-maze. If the rat is only allowed to investigate one arm of the maze in the first run it will tend to visit the other arm if given a second run, that is they will exhibit spontaneous alternation (Dember W.N., and Fowler H., Psychological Bulletin, 55, 412–428, 1985.)

Test Procedure

Each rat was given a single trial, consisting of 2 runs in an open T-maze which was constructed essentially as described by Salomone J. D., Beart, P. M., Alpert, J. E. and Iversen, S. D., Behav. Brain Res. 13, 63–70, 1984. On the first run, a wooden barrier was positioned across the entrance to one arm of the T-maze, allowing the animal to enter the opposite area only. After entering the side arm the rat was confined there for 30 seconds before being removed from the maze. After an 8 minute inter-run interval, the rat was positioned at the beginning of the start and allowed a free choice of either arm of the T-maze. The direction of choice was recorded and the percentage of correct alternations for a minimum of 10 rats per treatment per experiment was calculated. Tests were carried out using rats treated with the test compound, rats treated with scopolamine (a drug known to impair memory and disrupt spontaneous alternation) and rats treated with the test compound and scopolamine. In each test the treated rats were compared with saline treated animals.

Results

Administration of the test compound at 0.01 µg/kg s.c. twice a day over two days increased spontaneous alternation to 93% compared with 75–78% for saline treated animals. Administration of scopolamine at 0.25mg/kg i.p., twice a day over two days significantly impaired the spontaneous alternation to the 60% level compared with the 86% level of the saline treated control rats, whereas administration of the test compound at 0.001 µg/kg s.c. twice a day over two days to rats also treated with scopolamine 0.25 mg/kg i/p. twice a day over two days reversed the impairment produced by scopolamine to give spontaneous alternations of 90%.

Marmoset learning tasks in the Wisconsin General Test Apparatus

Introduction and Test Procedure

Common marmosets were tested for performance in a discriminative learning task and reverse learning task using the Wisconsin General Test apparatus described by Harlow H. F., Psychological Review, 56, 51–65, 1949. The experiments were essentially carried out following the experimental protocol of Baker H. F., Ridley R. M. and Drewett, B., Psychopharmacology, 91, 512–514, 1987. The test compound was administered into the hind leg of the marmoset as a subcutaneous (s.c.) injection in 1 ml of saline.

Results

Administration of the test compound at doses of 1 and 10 ng/kg s.c. twice a day throughout testing markedly improved the performance of the marmosets in the reverse learning task.

I claim:

1. A method for treatment of dementia and other cognitive disorders which comprises administering to a human or animal subject suffering from dementia or other cognitive disorders an effective amount for the treatment of said dementia or other cognitive disorders of 1,2,3,9,-tetrahydro-9-methyl-3-[(2-methyl-1H-imidazol-1-yl)methyl]-4H-carbazol-4-one or a physiologically acceptable salt or solvate thereof.

2. A method according to claim 1 wherein said 1,2,3,9,-tetrahydro-9-methyl-3-[(2-methyl-1H-imidazol-1-yl)methyl]-4H-carbazol-4-one is administered in the form of a hydrochloride salt.

3. A method according to claim 1 wherein said 1,2,3,9,-tetrahydro-9-methyl-3-[(2-methyl-1H-imidazol-1-yl)methyl]-4H-carbazol-4-one is administered in the form of the hydrochloride dihydrate salt.

4. A method according to claim 1 wherein said 1,2,3,9-tetrahydro-9-methyl-3-[(2-methyl-1H-imidazol-1-yl)methyl]-4H-carbazol-4-one or a physiologically acceptable salt or solvate thereof is administered in a dose of 0.5 µg to 20 mg from 1 to 4 times per day, the dose being expressed as the weight of free base.

5. A method according to claim 1 wherein said 1,2,3,9-tetrahydro-9-methyl-3-[)2-methyl-1H-imidazol-1-yl)methyl]-4H-carbazol-4-one or a physiologically acceptable salt or solvate thereof is administered in a dose of 0.05 mg to 20 mg from 1 to 4 times per day, the dose being expressed as the weight of free base.

6. A method according to claim 1 wherein said 1,2,3,9-tetrahydro-9-methyl-3-[(2-methyl-1H-imidazol-1-yl)methyl]-4H-carbazol-4-one is administered orally, buccally, parenterally, rectally, or as a depot preparation.

* * * * *

UNITED STATES PATENT AND TRADEMARK OFFICE
CERTIFICATE OF CORRECTION

PATENT NO.   :   4,845,115

DATED        :   July 4, 1989

INVENTOR(S)  :   Michael B. TYERS

It is certified that error appears in the above-identified patent and that said Letters Patent is hereby corrected as shown below:

On the title page, in §56, under "References Cited," please insert the following:

—U.S. PATENT DOCUMENTS

| | | |
|---|---|---|
| 4,753,789 | 6/1988 | Tyers et al |
| 4,721,720 | 1/1988 | Wootton et al |
| 4,624,961 | 11/1986 | Welstead, Jr.—; | under "FOREIGN PATENT DOCUMENTS" please insert the following:

| | | |
|---|---|---|
| — 2193633A | 2/1988 | United Kingdom |
| 190920 | 8/1986 | Europe —. |

Claim 1, line 6, delete "1,2,3,9,-" and insert — 1,2,3,9- —.

Claim 2, line 2, delete "1,2,3,9,-" and insert — 1,2,3,9- —.

Claim 3, line 2, delete "1,2,3,9,-" and insert — 1,2,3,9- —.

Claim 4, line 5, delete "0.5 µg" and insert —0.05 µg—.

Claim 5, line 2, delete "3-[)2-" and insert —3-[(2- —.

Signed and Sealed this

Twenty-eighth Day of August, 1990

Attest:

HARRY F. MANBECK, JR.

*Attesting Officer*    *Commissioner of Patents and Trademarks*